United States Patent [19]

Brown et al.

[11] 4,188,326

[45] * Feb. 12, 1980

[54] INDOLOPYRONES HAVING ANTI-ALLERGIC ACTIVITY

[75] Inventors: Richard E. Brown, Hanover, N.J.; Paul C. Unangst, Ann Arbor, Mich.

[73] Assignee: Warner-Lambert Company, Morris Plains, N.J.

[*] Notice: The portion of the term of this patent subsequent to Jun. 7, 1994, has been disclaimed.

[21] Appl. No.: 890,544

[22] Filed: Mar. 20, 1978

Related U.S. Application Data

[63] Continuation-in-part of Ser. No. 764,150, Jan. 31, 1977, abandoned, which is a continuation-in-part of Ser. No. 611,453, Sep. 8, 1975, Pat. No. 4,028,383.

[51] Int. Cl.² ............................................. C07D 491/04
[52] U.S. Cl. ...................... 260/326.29; 260/326.12 R; 260/326.13 C; 260/326.16; 124/274
[58] Field of Search ..................... 260/326.29

[56] References Cited

U.S. PATENT DOCUMENTS

| | | | |
|---|---|---|---|
| 4,028,383 | 6/1977 | Brown et al. | 260/326.29 |
| 4,036,842 | 7/1977 | Dobson et al. | 260/326.29 |
| 4,076,831 | 2/1978 | Demerson et al. | 260/326.29 |

OTHER PUBLICATIONS

Tominager et al.; Chem. Abs. vol. 80: 59885x (1974).
Tominager et al.; Chem. Abs. vol. 79: 105109b (1973).
Koberyashi et al.; Chem. Abs. vol. 79: 115396g (1973).

Primary Examiner—Donald G. Daus
Assistant Examiner—Mary Lee
Attorney, Agent, or Firm—Albert H. Graddis

[57] ABSTRACT

This invention relates to novel substituted indolopyrones which have utility in preventing allergic and asthmatic reactions in mammals.

11 Claims, No Drawings

INDOLOPYRONES HAVING ANTI-ALLERGIC ACTIVITY

This application is a continuation-in-part application of U.S. Ser. No. 764,150, filed Jan. 31, 1977, which in turn is a continuation-in-part application of U.S. Pat. Ser. No. 611,453, filed Sept. 8, 1975, and now U.S. Pat. No. 4,028,383.

This invention relates to substituted indolopyrones of the general formula:

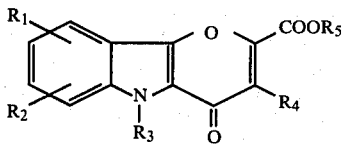

wherein $R_1$ and $R_2$ may be hydrogen, halogen, hydroxy, trifluoromethyl, lower alkoxy or lower alkyl of 1 to 6 carbon atoms; or may be taken together to form a methylenedioxy group; $R_3$ may be hydrogen, lower alkyl of 1 to 6 carbon atoms, phenyl or phenylmethyl; $R_4$ and $R_5$ may be hydrogen or lower alkyl of 1 to 6 carbon atoms in length, as well as their pharmaceutically acceptable salts.

The compounds of this invention may be prepared by one of the following reaction sequences:

In the first reaction sequence, an ester of a substituted indoxylic acid according to formula II is reacted with dimethylsulfone in the presence of a strong base, as, for example, sodium hydride, sodium amide, potassium methoxide, and the like to give the corresponding β-ketosulfone according to structure III wherein $R_4$ is hydrogen.

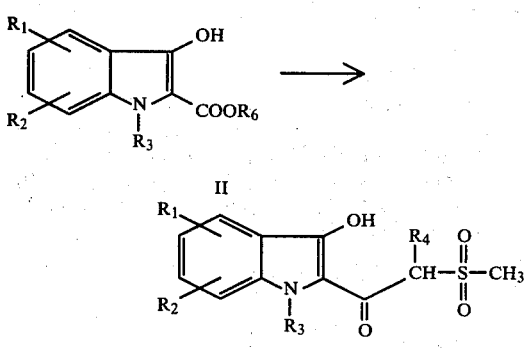

The reaction is conveniently carried out in a polar aprotic solvent as, for example, dimethylformamide, dimethyl sulfoxide, phentydrone and the like.

The substituted indoxylic acid esters are known compounds and are easily prepared by the methods described in the literature for this class of compounds. In structures II and III, $R_1$, $R_2$ and $R_3$ are as before defined; $R_6$ is a lower alkyl group of 1 to 6 carbon atoms.

In the second step, the β-ketosulfone of Structure III is treated with a lower alkyl halide or tosylate having 1 to 6 carbon atoms in the presence of a strong base and is thereby converted to a compound of structure III wherein $R_4$ is lower alkyl of 1 to 6 carbon atoms.

In the third step, the compound according to structure III is reductively cleaved to the compound of structure IV:

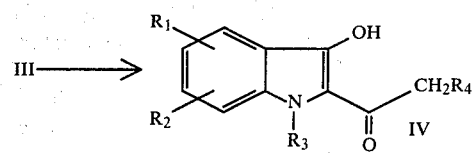

This reductive cleavage is best carried out with aluminum amalgam or zinc dust in the presence of a lower alkyl organic acid such as, for example, acetic acid.

In the fourth step, the compound of structure IV is reacted with a lower alkyl ester of oxalic acid, in the presence of a strong base, to give a compound according to structure I in which $R_1$, $R_2$, $R_3$, and $R_4$ are as defined and $R_5$ is a lower alkyl group of 1 to 6 carbon atoms. Among the strong bases which may be used for this reaction are sodium hydride, sodium amide, potassium t-butoxide, or, preferably, sodium ethoxide. The reaction of the fourth step is conveniently carried out in a solvent such as, for example, ethanol, dimethylformamide, dimethyl sulfoxide, phentydrone and the like.

In the final step, saponification of the ester of structure I wherein $R_5$ is a lower alkyl group of 1 to 6 carbon atoms is carried out to afford the acid of structure I, wherein $R_5$ is hydrogen.

It is believed that one of ordinary skill in the art, can, using the preceding description, utilize the first reaction sequence of the present invention to its fullest extent. The following specific embodiments, are, therefore, to be simply construed as merely illustrative and not to limit the remainder of the specification and claims in any way whatsoever.

EXAMPLE 1

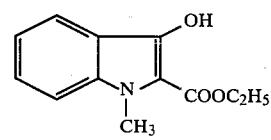

Ethyl-N-methylindoxylate

A mixture of 38.8 g (0.2 mole) of ethyl chloromalonate and 44 g (0.41 mole) of N-methylaniline was heated on the steam bath for 72 hours. After cooling, the mixture was diluted with 500 ml of methylene chloride and unreacted N-methylaniline extracted with 4 N HCl. The methylene chloride layer was dried and concentrated to 49 g of oil. This was diluted with 49 ml of hexamethylphosphoramide, and the mixture heated rapidly to boiling (bath temp. 245°). Reflux was continued for 20 minutes, the mixture cooled rapidly and poured into 400 ml of 4 N HCl. The crude solid product was filtered and recrystallized from isopropanol to give crystals, mp. 95°–6°.

EXAMPLE 2

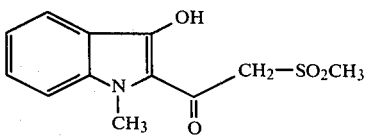

1-(3-hydroxy-1-methyl-1H-indol-2-yl)-2-(methylsulfonyl)ethanone

A solution of 56.4 g (0.60 mole) dimethyl sulfone in 300 ml dimethyl sulfoxide was added over 10 minutes to a nitrogen-filled flask containing 30.0 g (0.62 mole) of sodium hydride (previously washed with pet ether). After stirring and heating at 65°–75° for 75 minutes, the mixture was cooled to room temperature, and 100 ml of THF was added, followed by 43.8 g (0.20 mole) ethyl N-methyl indoxylate in 250 ml THF, added over 10 min. After heating an additional 2 hours at 65°–75°, the mixture was cooled and added to 2200 ml of 0.55 N ice cold HCl. After standing overnight, the product was filtered and recrystallized from methanol to give yellow needles, mpt. 168°–170°.

Anal. Calcd. for $C_{12}H_{13}NO_4S$: C, 53.92; H, 4.90; N, 5.24; S, 12.00. Found: C, 53.75; H, 4.99; N, 5.11; S, 12.04.

EXAMPLE 3

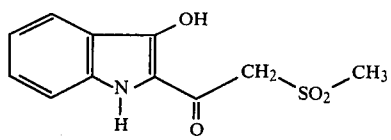

1-(3-Hydroxy-1H-indol-2-yl)-2-(methylsulfonyl)-ethanone

In a manner analogous to that of Example 2, the title compound was prepared from the known* methyl 3-hydroxy-indole-2-carboxylate. Two recrystallizations of the final product from methanol yielded yellow needles of mpt. 225°-dec.

*A. Robertson, *J. Chem. Soc.*, 1937 (1927).

Anal. Calc. for $C_{11}H_{11}NO_4S$: C, 52.17; H, 4.38; N, 5.53; S, 12.66. Found: C, 52.09; H, 4.39; N, 5.48; S, 12.66.

EXAMPLE 4

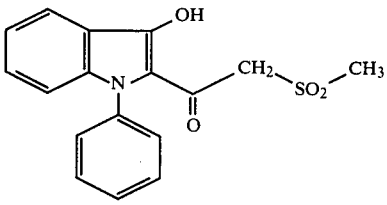

1-(3-Hydroxy-1-phenyl-1H-indol-2-yl)-2-(methylsulfonyl)ethanone

In a manner analogous to that of Example 2, the title compound was prepared from the known* methyl N-phenyl-indoxylate. An analytical sample was obtained by dissolving the methanol recrystallized product in chloroform, drying ($Na_2SO_4$), evaporating to a yellow semi-solid residue, and recrystallization of the residue from ethyl acetate. Cooling gave yellow cubes of mpt. 163°–166°.

*P. Friedlander and K. Krenz, *Ber.*, 55, 1597 (1922).

Anal. Calc. for $C_{17}H_{15}NO_4S$: C, 61.99; H, 4.59; N, 4.25; S, 9.74. Found: C, 61.98; H, 4.69; N, 4.23; S, 9.84.

EXAMPLE 5

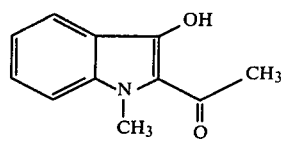

3-hydroxy-1-methyl-1H-indol-2-yl methyl ketone

A mixture of 17.0 g (0.0637 mole) 1-(3-hydroxy-1-methyl-1H-indol-2-yl)-2-(methylsulfonyl)ethanone, 21.0 g (0.32 mole) zinc dust, 40 ml glacial acetic acid and 80 ml ab. ethanol was stirred vigorously and heated at 45°–50° for 1 hour. After stirring an additional hour at room temperature, the mixture was filtered through diatomaceous earth and the filter cake washed several times with fresh ethanol. The combined filtrates were condensed to 150 ml and 50 ml of hot water was added. Cooling yielded a green solid which was filtered, washed with cold water and recrystallized from 70% aqueous methanol to yield green needles of mpt. 119°–121°.

Anal. Calcd. for $C_{11}H_{11}NO_2$: C, 69.82; H, 5.86; N, 7.40. Found: C, 69.56; H, 5.85; N, 7.24.

EXAMPLE 6

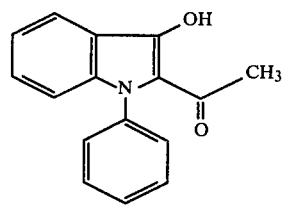

3-Hydroxy-1-phenyl-1H-indol-2-yl methyl ketone

In a manner analogous to that of Example 5, the title compound was prepared from 1-(3-hydroxy-1-phenyl-1H-indol-2-yl)-2-(methylsulfonyl)ethanone. The product was obtained as green needles of mpt. 127°–130° from the condensed ethanol-acetic acid filtrate by the addition of warm water, followed by slow cooling.

Anal. Calcd. for $C_{16}H_{13}NO_2$: C, 76.47, H, 5.22; N, 5.57. Found: C, 76.37; H, 5.41; N, 5.32.

EXAMPLE 7

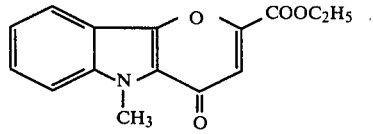

Ethyl 4,5-dihydro-5-methyl-4-oxopyrano[3,2-b]-indole-2-carboxylate

To a solution of 6.0 g (0.26 mole) of sodium metal in 600 ml ab. ethanol was added 18.0 g (0.095 mole) of 3-hydroxy-1-methyl-1H-indol-2-yl methyl ketone, followed by 37.6 g (0.26 mole) of diethyl oxalate, added over 10 min. The mixture was stirred and heated at reflux for 17 hours, cooled and the red di-sodium salt was filtered and washed with cold hexane. The crude salt was added to a solution of 28 ml conc. HCl and 120 ml ab. ethanol, heated at reflux for 30 min., and the mixture was filtered while hot. Cooling the filtrate gave the crude product, which was filtered and then dissolved in 400 ml of chloroform. The chloroform solution was washed 3 times with dilute aqueous NaHCO₃, 1 time with water, dried (MgSO₄) and evaporated to leave a grey residue. Recrystallization from 15% CHCl₃ in hexane gave yellow needles of mpt. 160°–162°.

Anal. Calcd. for $C_{15}H_{13}NO_4$: C, 66.41; H, 4.83; N, 5.16. Found: C, 66.59; H, 4.81; N, 4.94.

EXAMPLE 8

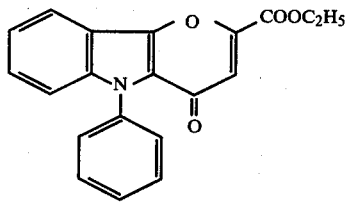

Ethyl-4,5-dihydro-4-oxo-5-phenylpyrano[3,2-b]indole-2-carboxylate

In a manner analogous to that of Example 7, the title compound was prepared from 3-hydroxy-1-phenyl-1H-indol-2-yl methyl ketone. Recrystallization from aqueous methanol followed by an additional recrystallization from ethyl acetate gave light pink needles of mpt. 192°–194°.

Anal. Calc. for $C_{20}H_{15}NO_4$: C, 72.06; H, 4.54; N, 4.20. Found: C, 72.05; H, 4.62; N, 4.17.

EXAMPLE 9

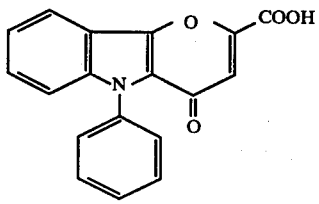

4,5-Dihydro-4-oxo-5-phenylpyrano[3,2-b]indole-2-carboxylic acid.

A mixture of 1.0 g (0.0033 mole) of ethyl 4,5-dihydro-4-oxo-5-phenylpyrano[3,2-b]indole-2-carboxylate in 10 ml glacial acetic acid and 2.0 ml conc. hydrochloric acid was stirred at reflux for 4½ hr, then cooled and added to 75 g ice—H₂O. The solid was filtered, washed with cold water, then added to a mixture of 35 ml 5% aqueous sodium carbonate and 250 ml water. After filtering by gravity, the aqueous solution was washed three times with 75 ml chloroform, cooled in ice, and acidified with 4.0 N hydrochloric acid. The orange precipitate was filtered, digested 15 min on the steam bath with 25 ml water and re-filtered warm. Recrystallization from DMF-water yielded an off-white solid of mpt. >290°.

Anal. Calcd. for $C_{18}H_{11}NO_4$: C, 70.81; H, 3.63; N, 4.59. Found: C, 70.77; H, 3.69; N, 4.49.

In the second reaction sequence, the compounds of this invention are prepared in a similar manner with the exception that the intermediate ketone IV(b) is prepared by reacting a substituted anthranilic acid of structure V with chloroacetone in the presence of a base.

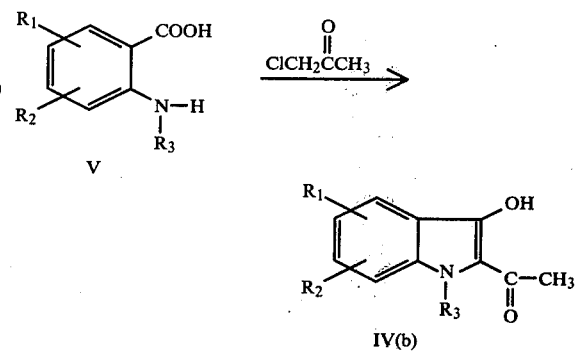

In structures V and IV(b), $R_1$ and $R_2$ may be hydrogen, hydroxy, lower alkoxy or lower alkyl of 1 to 6 carbon atoms, halogen, trifluoromethyl, or may be taken together to form a methylenedioxy group. $R_3$ may be hydrogen, lower alkyl of 1 to 6 carbon atoms, phenylmethyl, or a phenylalkylene group of 1 to 6 carbons in the chain. Preferably, however, $R_1$ and $R_2$ may be hydrogen, halogen, or lower alkyl of 1 to 6 carbon atoms, and $R_3$ may be lower alkyl of 1 to 6 carbon atoms or phenylmethyl.

The reaction of the substituted anthranilic acid with chloroacetone is described in U.S. patent application Ser. No. 764,110 in our names and in the names of Fontsere and Fabian, the disclosure being incorporated in toto into this disclosure.

It is believed that one of ordinary skill in the art, can, using the preceding description, utilize the second reaction sequence to its fullest extent. The following specific embodiments, are, therefore, to be simply construed as merely illustrative of the second reaction sequence to prepare the novel compounds of this disclosure and not to limit the remainder of the specification and claims in any way whatsoever.

EXAMPLE 10

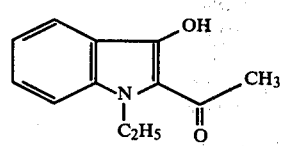

1-Ethyl-3-hydroxy-1H-indol-2-yl methyl ketone

A mixture of 35.0 g (0.212 mole) 2-ethyaminobenzoic acid, 30.0 g (0.217 mole) potassium carbonate, and 42.9 g (0.465 mole) distilled chloroacetone in 350 ml water and 150 ml ethanol was stirred at reflux for 90 min. The reaction mixture was cooled, stirred in ice for 1 hr, and the crude solid product was filtered and washed with cold water. After suspending the crude solid in 500 ml of 0.5 N aqueous NaOH, the mixture was digested with charcoal for 15 min on the steam bath and then filtered hot. The filtrate was cooled in ice and acidified with 4 N HCl. The green precipitate was filtered, washed with cold water, then digested (steam) briefly in 750 ml 5% aqueous NaHCO₃, refiltered and again washed with water. Several recrystallizations from aqueous methanol yielded yellow needles of mpt. 119.5°–121°.

Anal. Calcd. for $C_{12}H_{13}NO_2$: C, 70.91; H, 6.45; N, 6.89. Found: C, 70.70; H, 6.53; N, 6.86.

EXAMPLE 11

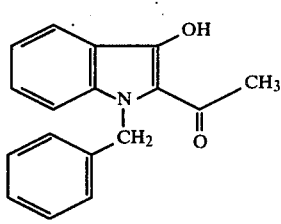

3-Hydroxy-1-phenylmethyl-1H-indol-2-yl methyl ketone

A mixture of 140 g (0.618 mole) 2-(phenylmethylamino)benzoic acid, 43.0 g (0.311 mole) potassium carbonate, and 60 g (0.650 mole) distilled chloroacetone in 900 ml water and 400 ml ethanol was stirred at reflux for 18 hr. The cooled reaction mixture was treated in the manner described in Example 10. Several recrystallizations of the final product from aqueous methanol yielded light green needles of mpt. 149.5°–151.5°.

Anal. Calcd. for $C_{17}H_{15}NO_2$: C, 76.96; H, 5.70; N, 5.28. Found: C, 76.81; H, 5.80; N, 5.27.

EXAMPLE 12

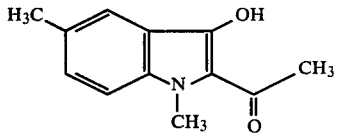

1,5-Dimethyl-3-hydroxy-1H-indol-2-yl methyl ketone

In a manner analogous to that of Example 10, the title compound was prepared from 5-methyl-2-methylaminobenzoic acid. Several recrystallizations of the final product from aqueous methanol yielded yellow flakes of mpt. 120°–122°.

Anal. Calcd. for $C_{12}H_{13}NO_2$: C, 70.91; H, 6.45; N, 6.89. Found: C, 70.87; H, 6.43; N, 7.02.

EXAMPLE 13

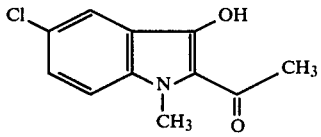

5-Chloro-3-hydroxy-1-methyl-1H-indol-2-yl methyl ketone

In a manner analogous to that of Example 10, the title compound was prepared from 5-chloro-2-methylaminobenzoic acid. Several recrystallizations of the final product from aqueous methanol yielded a green solid of mpt. 177°-dec.

Anal. Calcd. for $C_{11}H_{10}ClNO_2$: C, 59.07; H, 4.51; N, 6.26; Cl, 15.85. Found: C, 58.95; H, 4.59; N, 6.09; Cl, 15.75.

EXAMPLE 14

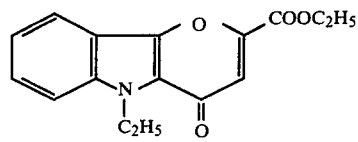

Ethyl-4,5-dihydro-5-ethyl-4-oxopyrano[3,2-b]indole-2-carboxylate

In a manner analogous to that of Example 7, the title compound was prepared from 3-hydroxy-1-ethyl-1H-indol-2-yl methyl ketone. The initial red disodium salt intermediate was isolated by removal of the bulk of the reaction solvent under vacuum and addition of excess cold ether or hexane to the residue. Recrystallization of the final product from 10% aqueous methanol yielded tan needles of mpt. 169°–171°.

Anal. Calcd. for $C_{16}H_{15}NO_4$: C, 67.36; H, 5.30; N, 4.91. Found: C, 67.26; H, 5.32; N, 4.84.

EXAMPLE 15

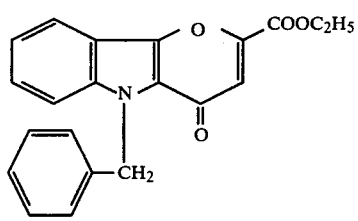

Ethyl-4,5-dihydro-4-oxo-5-(phenylmethyl)pyrano[3,2-b]indole-2-carboxylate

In a manner analogous to that of Example 7, the title compound was prepared from 3-hydroxy-1-phenylmethyl-1H-indol-2-yl methyl ketone (Example 11). Recrystallization from 10% aqueous methanol yielded grey needles of mpt. 135°–137° C.

Anal. Calcd. for $C_{21}H_{17}NO_4$: C, 72.61; H, 4.93; N, 4.03. Found: C, 72.56; H, 4.96; N, 3.92.

EXAMPLE 16

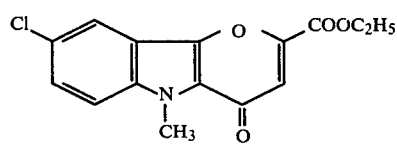

Ethyl-8-chloro-4,5-dihydro-5-methyl-4-oxopyrano[3,2-b]indole-2-carboxylate

In a manner analogous to that of Example 7, the title compound was prepared from 5-chloro-3-hydroxy-1-methyl-1H-indol-2-yl methyl ketone. Recrystallization two times from methanol yielded yellow needles of mpt. 170°–172°.

Anal. Calcd. for $C_{15}H_{12}ClNO_4$: C, 58.93; H, 3.96; N, 4.58; Cl, 11.60. Found: C, 58.65; H, 3.94; N, 4.46; Cl, 11.67.

EXAMPLE 17

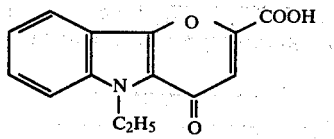

5-Ethyl-4,5-dihydro-4-oxopyrano[3,2-b]indole-2-carboxylic acid

The red disodium salt intermediate from Example 14 (8.5 g, 0.025 mole) was stirred at reflux for 90 minutes in a mixture of 50 ml. glacial acetic acid and 10 ml conc. hydrochloric acid. After cooling and addition to 500 g ice—H$_2$O, the dark solid precipitate was filtered and washed with cold water. The crude product was dissolved in 40 ml 1.0 N aqueous sodium hydroxide and an additional 20 ml of water was added. The aqueous solution was washed three times with 40 ml of methylene chloride, then cooled in ice and acidified with 4.0 N hydrochloric acid. Filtration of the brown solid, followed by washing with water and two recrystallizations of the dried product from ethyl acetate yielded a tan solid of mpt. 275°-dec.

Anal. Calcd. for C$_{14}$H$_{11}$NO$_4$: C, 65.36; H, 4.31; N, 5.45. Found: C, 65.21; H, 4.27; N, 5.40.

EXAMPLE 18

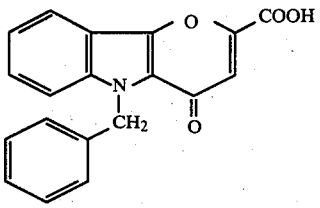

4,5-Dihydro-4-oxo-5(phenylmethyl)pyrano[3,2-b]indole-2-carboxylic acid

A mixture of 6.0 g (0.017 mole) of ethyl 4,5-dihydro-4-oxo-5-(phenylmethyl)pyrano[3,2-b]indole-2-caroboxylate, 80 ml 1% aqueous sodium hydroxide, and 450 ml water was stirred at room temperature for 3 hr. Ethanol (~150 ml) was then added until virtually all of the insoluble material present had dissolved. After washing twice with 250 ml of chloroform, the aqueous layer was filtered by gravity, cooled in ice, and acidified with 4 N hydrochloric acid. The tan precipitate was filtered, digested for 15 min on the steam bath with 100 ml of water and re-filtered while still warm. Recrystallization of the final product from DMF-water yielded a white powder of mpt. 290°-dec.

Anal. Calcd. for C$_{19}$H$_{13}$NO$_4$: C, 71.47; H, 4.10; N, 4.39. Found: C, 71.21; H, 4.24; N, 4.38.

EXAMPLE 19

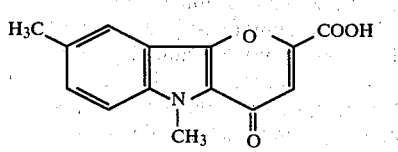

4,5-Dihydro-5,8-dimethyl-4-oxopyrano[3,2-b]indol-2-carboxylic acid

In a manner analogous to that of Example 14, 8.2 g (0.040 mole) of 1,5-dimethyl-3-hydroxy-1H-indol-2-yl methyl ketone (Example 12) was reacted with sodium metal (3.7 g, 0.16 mole) and diethyl oxalate (21.5 g, 0.20 mole) in 200 ml absolute ethanol. The red disodium salt intermediate was then converted to the title compound as described in Example 17. Two recrystallizations of the final product from DMF-water yielded yellow needles of mpt. 290°.

Anal. Calcd. for C$_{14}$H$_{11}$NO$_4$: C, 65.36; H, 4.31; N, 5.45. Found: C, 64.71; H, 4.38; N, 5.35.

EXAMPLE 20

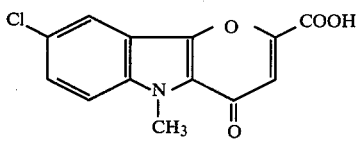

8-Chloro-4,5-dihydro-5-methyl-4-oxopyrano[3,2-b]indole-2-carboxylic acid

A mixture of 3.5 g (0.012 mole) of ethyl 8-chloro-4,5-dihydro-5-methyl-4-oxopyrano[3,2-b]indole-2-carboxylate in 50 ml glacial acetic acid and 10 ml conc. hydrochloric acid was stirred at reflux for 3 hr, then cooled and added to 500 g ice—H$_2$O. The crude product was filtered, washed with 50% aqueous ethanol, and air dried. A suspension of the product in 75 ml of chloroform was stirred for 90 min at room temperature, then filtered. After recrystallization twice from DMF-water, the final product was dried for several hours under high vacuum at 100°. The yellow flakes obtained had a mpt. of 290°-dec.

Anal. Calcd. for C$_{13}$H$_8$ClNO$_4$: C, 56.24; H, 2.90; N, 5.05; Cl, 12.77. Found: C, 56.10; H, 3.14; N, 5.01; Cl, 13.04.

In another aspect of the invention there is provided a pharmaceutical composition comprising a compound of Formula I as has been defined or a pharmaceutically acceptable salt thereof together with any of the conventional pharmaceutically acceptable carriers or excipients.

The pharmaceutically acceptable salts of the compounds in general Formula I may be prepared by conventional reactions with equivalent amounts of organic or inorganic solutions. As exemplary, but not limiting, of pharmaceutically acceptable salts are the salts of hydrochloric, hydrobromic, sulfuric, benzenesulphonic, acetic, fumaric, oxalic, malic and citric acids, and hydroxides of potassium and sodium.

The compositions may be administered parenterally in combination with conventional injectable liquid carriers such as sterile pyrogen-free water, sterile peroxide-free ethyl oleate, dehydrated alcohol or propylene glycol. Conventional pharmaceutical adjuvants for injection solutions such as stabilizing agents, solubilizing agents and buffers, for example, ethanol, complex form agents such as ethylene diamine tetraacetic acid, tartrate and citrate buffers and high-molecular weight polymers such as polyethylene oxide for viscosity regulation may be added. Such compositions may be injected intramuscularly, intraperitoneally, or intravenously.

The compositions may also be formulated into orally administratable compositions containing one or more physiologically compatible carriers or excipients, and may be solid or liquid in form. These compositions may, if desired, contain conventional ingredients such as binding agents, for example, syrups, acacia, gelatin, sorbitol, tragacanth, or polyvinylpyrollidone; fillers, for example, lactose, mannitol, starch, calcium, phosphate, sorbitol or methylcellulose; lubricants, for example, magnesium stearate, high-molecular weight polymers such as polyethylene glycols, high-molecular weight fatty acids such as stearic acid or silica, disintegrants, for example, starch; acceptable wetting agents as, for example, sodium lauryl sulfate. These compositions may take any convenient form, for example, tablets, capsules, lozenges, aqueous or oily suspensions, emulsions, or dry products suitable for reconstitution with water or other liquid medium before use. The liquid oral forms of administration may, of course, contain flavors; sweeteners; preservatives, for example, methyl or propyl p-hydroxybenzoates; suspending agents, for example, sorbitol, glucose or other sugar syrup, methyl, hydroxymethyl, or carboxymethyl celluloses, or gelatin; emulsifying agents as, for example, lecithin or sorbitan monooleate; or thickening agents. Non-aqueous compositions may also be formulated which comprise edible oils as, for example, fish-liver or vegatable oils. These liquid compositions may conveniently be encapsulated in, for example, gelatin capsules in a unit dosage amount.

The compositions may also be administered topically as an aerosol.

A particular aspect of this invention comprises a compound of Formula I in an effective unit dose form. By "effective unit dose" is meant a predetermined amount sufficient to be effective to bring about the desired antiallergic effect.

Any yet in a further aspect of the invention there is provided a method of producing an antiallergic reaction in mammals, including man, which comprises the administration of an effective antiallergic amount of a compound of Formula I or a pharmaceutically acceptable salt thereof.

The dosage of the compounds of Formula I or their pharmaceutically acceptable salts depends, of course, on the nature and severity of the biological reaction to be countered, as well as the path of administration.

The compounds of this invention are useful in the prevention of allergic and asthmatic reactions in mammals. For example, in tests conducted following the procedures of I. Mota, *Life Sciences,* 7:465 (1963) and Z. Ovary, *Proc. Soc. Exptl. Biol. Med.,* 81: 584 (1952), these compounds were capable of protecting rats from allergic and asthmatic reactions at dose levels of 0.5 to 5.0 mg/kg when administered parenterally and at a dose level of 0.1 to 1.0 mg/kg when administered intravenously. The passive cutaneous anaphylaxis procedure of Brocklehurst (Handbook of Experimental Immunology, Blackwell Scientific Publishing Co., Oxford) also showed these compounds to have antiallergic capabilities when administered intrapertioneally, intravenously or orally. The following table compares various active dosages and routes of administration for a number of compounds according to this invention when tested in the procedure according to Brocklehurst.

| Compound   | Dose | Route |
|------------|------|-------|
| Example 17 | 1.0  | IV    |
| Example 17 | 2.0  | PO    |
| Example 18 | 0.50 | IV    |
| Example 9  | 1.0  | IV    |
| Example 9  | 2.0  | PO    |
| Example 20 | 5.0  | IP    |
| Example 19 | 1.0  | IV    |
| Example 19 | 2.0  | PO    |

Having thus described our invention and the manner and process of making and using it in such full, clear, concise and extract terms as to enable any person skilled in the art to which it pertains, or with which it is most nearly connected, to make and use the same, and having set forth the best modes for carrying out our invention, we claim:

1. A compound of the formula:

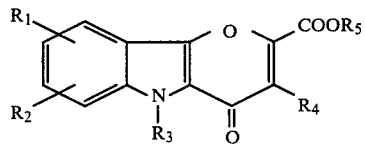

wherein $R_1$ and $R_2$ are hydrogen, halogen, hydroxy, trifluoromethyl, lower alkoxy or lower alkyl of 1 to 6 carbons, or may be taken together to form a methylenedioxy group; wherein $R_3$ is hydrogen, lower alkyl of 1 to 6 carbons, phenyl, or phenylmethyl; wherein $R_4$ is hydrogen; and wherein $R_5$ is hydrogen or lower alkyl of 1 to 6 carbons.

2. The compound according to claim 1 wherein $R_1$ and $R_2$ are hydrogen, hydroxy, halogen, lower alkoxy or lower alkyl of 1 to 6 carbons; wherein $R_3$ is hydrogen, lower alkyl of 1 to 6 carbons, phenyl, or phenylmethyl; wherein $R_4$ is hydrogen; and wherein $R_5$ is hydrogen or lower alkyl of 1 to 6 carbons.

3. The compound of claim 2 which is 4,5-dihydro-4-oxo-5(phenylmethylpyrano[3,2-b]indole-2-carboxylic acid.

4. The compound of claim 2 which is 8-chloro-4,5-dihydro-5-methyl-4-oxopyrano[3,2-b]indole-2-carboxylic acid.

5. The compound of claim 2 which is ethyl-8-chloro-4,5-dihydro-5-methyl-4-oxopyrano[3,2-b]indole-2-carboxylate.

6. The compound of claim 2 which is ethyl-4,5-dihydro-4-oxo-5-phenylpyrano[3,2-b]indole-2-carboxylate.

7. The compound of claim 2 which is ethyl-4,5-dihydro-5-ethyl-4-oxopyrano[3,2-b]indole-2-carboxylate.

8. The compound of claim 2 which is ethyl-4,5-dihydro-4-oxo-5-(phenylmethyl)pyrano[3,2-b]indole-2-carboxylate.

9. The compound of claim 2 which is 4,5-dihydro-5,8-dimethyl-4-oxopyrano[3,2-b]indole-2-carboxylic acid.

10. The compound of claim 2 which is 5-ethyl-4,5-dihydro-4-oxopyrano[3,2-b]indole-2-carboxylic acid.

11. The compound of claim 2 which is 4,5-dihydro-4-oxo-5-phenylpyrano[3,2-b]indole-2-carboxylic acid.

* * * * *